United States Patent [19]
Collins

[11] Patent Number: 5,208,581
[45] Date of Patent: May 4, 1993

[54] HIGH SPEED COMMUNICATION APPARATUS FOR COMPUTERIZED AXIAL TOMOGRAPHY (CAT) SCANNERS WITH MATCHING RECEIVER

[75] Inventor: Arthur K. Collins, Waukesha, Wis.

[73] Assignee: General Electric Company, Milwaukee, Wis.

[21] Appl. No.: 796,162

[22] Filed: Nov. 22, 1991

[51] Int. Cl.$^5$ ............................................. G08B 21/00
[52] U.S. Cl. ........................................ 340/671; 378/4; 378/15; 310/232
[58] Field of Search ................... 340/671, 672; 378/4, 378/15, 101; 310/232, 268, 166

[56] References Cited

U.S. PATENT DOCUMENTS

| | | | |
|---|---|---|---|
| 4,063,792 | 12/1977 | Lodge | 378/15 |
| 4,144,437 | 3/1979 | Albert | 378/19 |
| 4,201,430 | 5/1980 | Dimwiddie et al. | 378/15 |
| 4,329,004 | 5/1982 | Lewis | 378/15 |
| 4,644,573 | 2/1987 | Palermo et al. | 378/15 |
| 5,018,174 | 5/1991 | Collins | 378/4 |
| 5,055,821 | 10/1991 | Keller et al. | 378/15 |
| 5,109,397 | 4/1992 | Gordon et al. | 378/4 |

Primary Examiner—Jin F. Ng
Assistant Examiner—Niuen Tong
Attorney, Agent, or Firm—Quarles & Brady

[57] ABSTRACT

A high speed communication apparatus for a Computerized Axial Tomography (CAT) scanner utilizes large diameter slip rings to permit continuous rotation of a rotatable gantry. A communication signal is applied at a first point on one slip ring, and is terminated by a resistive termination point 180° opposite the driving point. The communication signal may then be received at any point on the slip ring by a receive connection and a matching receive connection which are 180° opposite one another. The drive and termination connections to the slip ring may be made by brushes, with the receive and matching receive connections being made by a physical connection to the slip ring. Alternately, the drive and terminate connections may be made by physical contact, with the receive and matching receive connections being made by brushes.

9 Claims, 4 Drawing Sheets

HIGH SPEED COMMUNICATION APPARATUS FOR COMPUTERIZED AXIAL TOMOGRAPHY (CAT) SCANNERS WITH MATCHING RECEIVER

BACKGROUND OF THE INVENTION

The field of the invention is Computerized Axial Tomography (CAT) scanners, and more particularly, CAT scanners of the type employing a gantry adapted for continuous rotation.

CAT scanners utilize a rotating gantry to obtain multiple X-ray images, or "views", at progressively different rotational angles. Each set of images is referred to in the art as a "slice". A patient is disposed in a central opening of the gantry on a table which is movable axially, thereby enabling slices to be obtained at multiple axial positions as well. All of the slices obtained are then processed in a computer according to known algorithms to produce enhanced images for diagnostic purposes.

The rotating gantry includes an X-ray apparatus and electronics necessary to generate image data for each view. It is therefore necessary to supply electrical power to the rotating gantry to power the electronics, and particularly to provide a high voltage supply for operation of the X-ray tube. Additionally, it is necessary to provide for communication of the image data, and other control information, between the electronics on the rotating gantry and a set of stationary electronics. The stationary electronics then process the raw image data into the enhanced form.

The data rate for communication between the stationary and rotating electronics is an important factor because it is desirable to obtain the desired views as fast as possible to reduce patient discomfort and to maximize equipment utilization. A view typically comprises 730 channels, with a 16 bit representation for each individual channel output (i.e. 11.68K bits per view) and is typically repeated 1,000 times per second, yielding a net data rate requirement of approximately 12 Megabits per second (Mbits/sec) for image data alone.

In order to provide a communications link with the requisite data rate, prior CAT scanners have employed an umbilical cable connected to the rotating gantry. One or more flexible, shielded coaxial cables are used in the umbilical cable for high speed communications, and other conductors are used for power and discrete control signals. The umbilical cable is typically capable of plus or minus 360° of rotation, so that the gantry is limited to a total of 720° of rotation. In operation, the gantry is accelerated to a desired rotational speed and the desired views are taken before the 720° limit is reached. Near the 720° limit, the gantry is decelerated to a stop, and then accelerated in the reverse direction to acquire more views. The gantry thus cycles back and forth within the 720° limit.

Such "cycling" type CAT scanners have two main disadvantages. One disadvantage is that the decelerating and re-accelerating of the gantry is fairly time consuming. The gantry, with all equipment in place, is both large and massive, so that even with large motors, the time consumed in accelerating the gantry can be substantial. The second disadvantage is somewhat of a corollary to the first, in that the need to repeatedly accelerate such a large mass produces a large amount of mechanical stress and wear.

Another type of gantry is known in the art in which brush and slip rings are used for power and communications. In these, the gantry is free to rotate continuously, eliminating the need for the above described back-and-forth movement of the gantry and thereby providing a greater proportion of time for the acquisition of the desired views. However, prior CAT scanners utilizing brushes and slip rings for communications have suffered a serious limitation of the data rates which can be achieved. This is due to the substantial time required to propagate the signals around the circular slip rings. At the desired data rates, the electrical path length around the rings is an appreciable fraction of a bit period, so that energy propagating around the rings in opposite directions may arrive at a reception point at substantially different times in a bit period, causing garbled reception.

U.S. Pat. No. 5,018,174 issued to Collins is another type of gantry in which brush and slip rings are used for power and communication. Again, this gantry design is limited in the data transmission rates achievable. The capacitance of the receive circuitry and the terminals that connect the receive circuitry with the slip rings causes an added delay of the signal on one-half of the slip ring transmission path resulting in signal energy being reflected at the termination means. These reflections further limit the maximum data transmission rates achievable.

Therefore, a need continues to exist for a high speed communications apparatus for a CAT scanner which provides for both continuous rotation and for reliable, higher speed communications.

SUMMARY OF THE INVENTION

A communications apparatus according to the invention provides high speed communications between first and second electronics systems mounted on first and second mechanical mounting structures, respectively. The first and second mechanical mounting structures rotate with respect to each other along an axis of rotation and a slip ring is arranged coaxially with the axis of rotation between the first and second mounting structures. The first electronics system is coupled to a drive means which makes electrical contact with the slip ring at a first point in the frame of reference of the first mounting structure, and termination means is mounted on the first mounting structure for providing passive termination of the electrical signal voltage on the slip ring at a point located approximately diametrically opposite said first point. Receive means is connected to the second electronic system and mounted on the second mechanical mounting structure for receiving the electrical signal voltage on the slip ring. The receive means makes electrical connection with the slip ring at a first point in the frame of reference of the second mechanical mounting structure and a matching receive means is mounted on the second mechanical mounting structure and makes electrical connection with the slip ring at a point approximately diametrically opposite (i.e. 180°) the receive means.

A general object of the invention is to provide very high data rate communications across a large diameter slip ring. The resistive termination, at a point diametrically opposite the driving point, electrically separates the slip ring into two paths around the ring, each of which is terminated. Energy traveling around the ring in opposite directions meets at the termination, mutually cancelling with no reflected energy or energy fed through to the other path. In addition, the matching receive means, at a point diametrically opposite the receive means, provides for a signal delay on its side of the slip ring transmission path approximately equal to the delay caused by the receive means. As a result, substantially no signal energy is reflected at the termination means thus further increasing the data transmission rates which are achievable.

For the best suppression, the resistive termination may have an impedance approximately equal to the impedance of the slip ring as seen at its connection point. Additionally, the driving means may have a source impedance approximately equal to the impedance of the slip ring as seen at its connection point.

The connections to the slip ring can take a variety of forms. If the first slip ring is mounted on the second mechanical mounting structure in a fixed position with respect to the frame of reference of the second mechanical mounting structure, then the first electronics system and the termination means make slidable electrical contact with the slip ring through brush contacts. Alternately, the first slip ring may be mounted on the first mechanical mounting structure in which case the receive means and the matching receive means make connection with the slip ring through brush contacts.

For example, the slip rings may be mounted on a gantry which rotates with respect to a stationary frame. By utilizing various combinations of brush and physical contact, both inbound (e.g. stationary to rotating) and outbound (e.g. rotating to stationary) communications may be implemented. In the case of the communication from the stationary frame to the rotating gantry, the stationary frame would be considered the first mechanical mounting structure, and the first and second connections for the driver and termination, respectively, would be by means of brushes. The third connection to the receiver and the fourth connection to the matching receiver would then be by means of physical electrical contacts. In the opposite case of communication from the rotating gantry to the stationary frame, the gantry would be considered the first mechanical mounting structure. The driver and termination would be on the rotating gantry, hence the first and second connections to the slip ring would be by means of physical electrical contact. The receiver and the matching receiver would be on the stationary frame hence the third and fourth connections would then be by means of brushes. The above recited examples are by no means inclusive of all possible combinations of slip ring and mounting and connections thereto. As a further example, instead of mounting the slip rings on the rotating gantry, the slip rings may alternately be fixed onto the stationary frame, or may even be free wheeling, e.g. not fixed to either mounting structure.

In order to have the first slip ring more closely approximate transmission line properties, a second slip ring may be provided. The second slip ring may be mounted coaxially with the first slip ring and arranged adjacent to the first slip ring. The drive means may include fifth connection means for making contact with the second slip ring at a third point in the frame of reference of the first mechanical mounting structure for applying the signal ground reference potential to the second slip ring, the third point being approximately collinear with the first point in the frame of reference of the first mechanical mounting structure. The termination means may include a sixth connection means for making contact with the second slip ring at a fourth point in the frame of reference of the first mechanical mounting structure, with the fourth point being approximately collinear with the second point in the frame of reference of the first mechanical mounting structure. The third and fourth points in the frame of reference of the first mechanical mounting structure are therefore approximately diametrically opposite each other across the second slip ring. The signal ground reference potential used for the resistive termination may then be obtained from the sixth connection means.

The receive means includes a seventh connection means for making contact with the second slip ring at a third point in the frame of reference of the second mechanical mounting structure. The first and third points in the frame of reference of the second mechanical mounting structure are approximately collinear. The matching receive means includes an eighth connection means for making contact with the second slip ring at a fourth point in the frame of reference of second mounting structure. The second and fourth points in the frame of reference of the second mounting structure are approximately collinear. In addition, the third and fourth points in this same frame of reference are approximately diametrically opposite each other across the second slip ring.

An object of the invention is to suppress extraneous noise on the slip rings to enhance reliable communications at high data rates. The fifth and sixth connection means may be coupled to a chassis ground reference potential through a capacitive bypass means, thereby providing a common sink for a.c. noise signals on the slip rings.

Another object of the invention is to provide substantial rejection of common mode noise by utilizing a third slip ring, in conjunction with the second slip ring, to supply an operating voltage to the receive means. The third slip ring is mounted coaxially with the first and second slip rings, with the first slip ring being arranged adjacent to and between the second and third slip rings. The drive means includes ninth connection means for making contact with the third slip ring at a fifth point in the frame of reference of the first mechanical mounting structure for applying a power supply voltage to the third slip ring. The power supply voltage is referenced to the signal ground reference potential on the second slip ring. The first, third and fifth points in the frame of reference of the first mechanical mounting structure are all approximately collinear. The termination means include a tenth connection means for making contact with the third slip ring at a sixth point in the frame of reference of the first mechanical mounting structure, with the sixth point being collinear with the second and fourth points in the same frame of reference and the fifth and sixth points in the same frame of reference are approximately opposite each other across the third slip ring. The signal ground reference potential used for the resistive termination may then be obtained from the tenth connection means. The receive means includes a eleventh connection means for making contact with the third slip ring at a fifth point in the frame of reference of the second mechanical mounting structure, with the fifth point being approximately collinear with the first and third points in the same frame of reference. The matching receiver means includes a twelfth contact means for making contact with the third slip ring at a sixth point in the frame of reference of the second mechanical mounting structure; the sixth point is approximately collinear with the second and fourth points in the same frame of reference. In addition, the fifth and sixth points in the frame of reference of the second mechanical mounting structure are approximately diametrically opposite each other across the third slip ring.

Consequently, an operating voltage for the receive means and matching receive means is obtained as the voltage between the power supply voltage obtained from the eleventh or twelfth connection means respectively and the signal ground reference potential obtained from the seventh or eighth connection means, respectively. This technique for supplying an operating voltage to the receive means is particularly advantageous in that common mode noise, i.e. noise introduced into all three slip rings, has negligible effect on the receive means, even though the receive means may be formed using less expensive single ended, i.e. non-differential, components.

The foregoing and other objects and advantages of the invention will appear from the following description. In the description, reference is made to the accompanying drawings which form a part hereof, and in which there is shown by way of illustration a preferred embodiment of the invention. Such embodiment does not represent the full scope of the invention, however, and reference is made therefore to the claims herein for interpreting the scope of the invention.

GENERAL DESCRIPTION OF THE INVENTION

Figure 1:
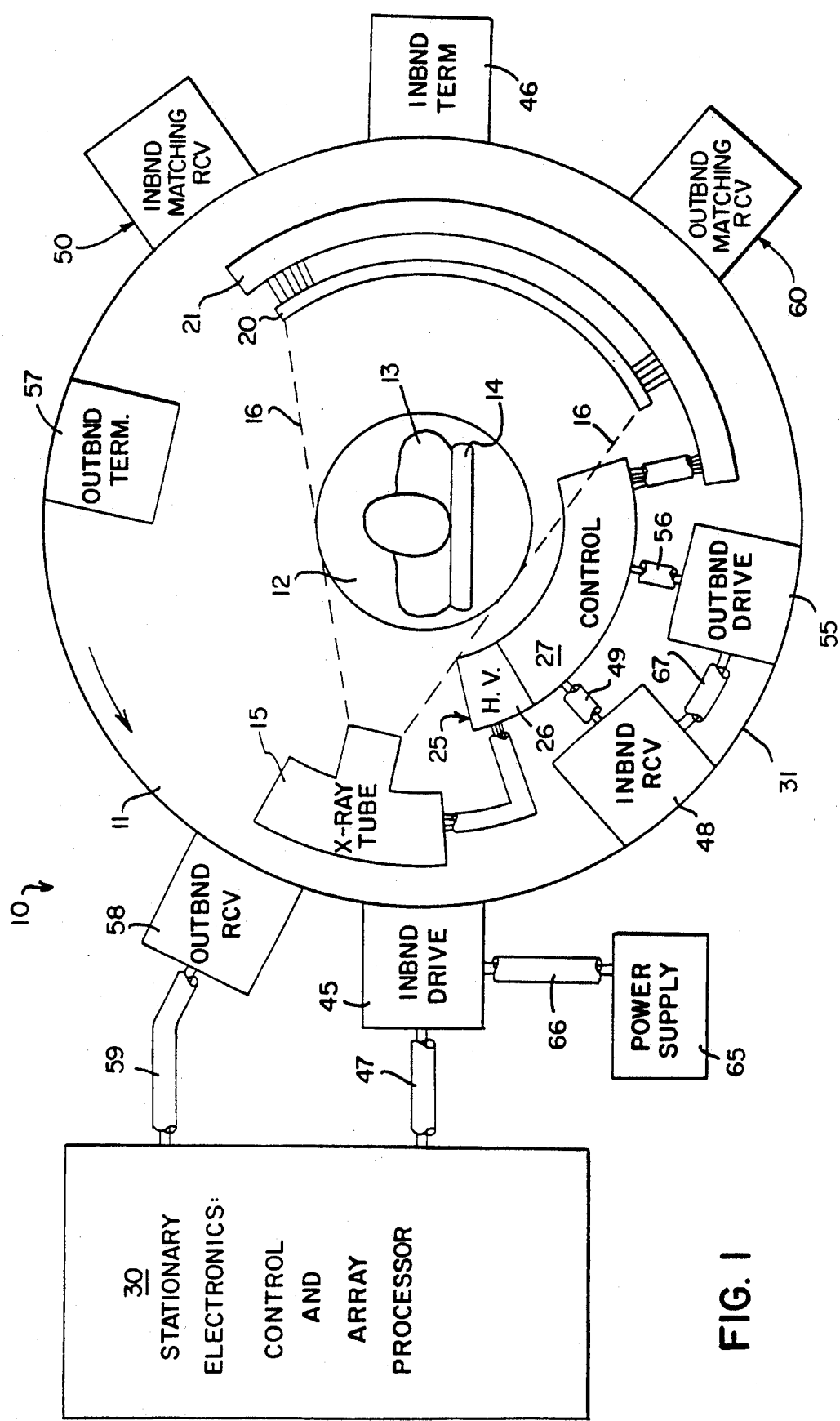
FIG. 1 is block diagram of a Computerized Axial Tomography (CAT) scanner which employs the high speed communication apparatus of the present invention.

Referring to FIG. 1, a Computerized Axial Tomography (CAT) scanner 10 includes a rotating gantry 11 with a central opening 12 large enough to receive a human patient 13. The patient 13 is supported on a table 14 which is slidable axially, e.g. in and out through the central opening 12. The gantry 11 also includes an X-ray tube 15 with associated beam shaping apparatus for producing a thin, fan shaped X-ray beam, shown generally by dotted lines 16. The beam 16 passes across the central opening 12, through the patient 13 disposed therein, and impinges on a detector array 20. The detector array 20 is curvilinear, with 730 channel resolution along its length. The individual outputs of each channel in the detector array 20 are connected in parallel to a data acquisition system 21, or DAS as it is referred to in the art. When sampled, each channel output is converted by the DAS to a 16 bit digital value representing X-ray intensity.

The gantry 11 further includes an on-board electronics system, represented generally by reference numeral 25. The on-board electronics rotates along with the gantry 11 and includes the necessary circuitry for operation of the X-ray tube 15 and collection of the image data acquired by the DAS 21. Specifically, the electronics system includes a high voltage section 26 and a control section 27. The control section 27 includes a computer (not shown), which is essentially a slave to stationary electronics system 30, the latter of course being located off the gantry 11. The stationary electronics system 30 is a computer based system for issuing commands to the control section 27 on the gantry 11 and for accepting and processing the resulting image data.

The present invention is directed to a communication system linking the stationary electronics 30 with rotating control section 27 through the use of large diameter slip rings and brushes which allow continuous rotation of the gantry 11. As discussed above, the minimum data rate required for image data alone is on the order of 12 Mbits/sec. an aggregate data rate of 88 Mbits/sec is communications data in addition to image data on a time multiplexed basis, as well as to account for communications overhead. High data rates have heretofore not been possible with large diameter slip rings. The present invention overcomes this limitation by allowing extremely high speed communication, even with the large diameter slip rings of a CAT scanner.

In the discussion which follows, it is assumed that all of the communication between the stationary electronics 30 and the control section 27 on the gantry 11 has been serialized, e.g. converted from parallel to serial data for transmission and vice versa on reception, using known multiplexing techniques. This is done so that only a single bit stream need be transmitted, although it should be apparent to those skilled in the art that multiple parallel paths according to the invention could be employed, for example, to further increase the maximum data rate attainable.

As will be described in detail below, several sets of slip rings and brushes are actually employed in this preferred embodiment. However, for the sake of simplicity, the slip rings in general are represented in FIG. 1 by circle 31 which defines the outer boundary of the gantry 11. Conventional brushes (not explicitly shown in FIG. 1) are employed for applying electrical energy, modulated to represent the serial data to be communicated, onto the slip rings represented at 31.

The size of the slip rings 31 is preferably on the order of four feet in diameter, or approximately 12.56 feet in circumference. Further, the bandwidth required to reliably transmit at the preferred data rate of 88 Mbits/sec, including modulation sidebands, is on the order of 400 Mhz. Because of the large physical size of the slip rings and the extremely high data rates involved, and the correspondingly fast rise times, or edge rates required, the slip rings 31 are treated as high frequency transmission lines, which may be modeled as shown in FIG. 1a.

Figure 1A:
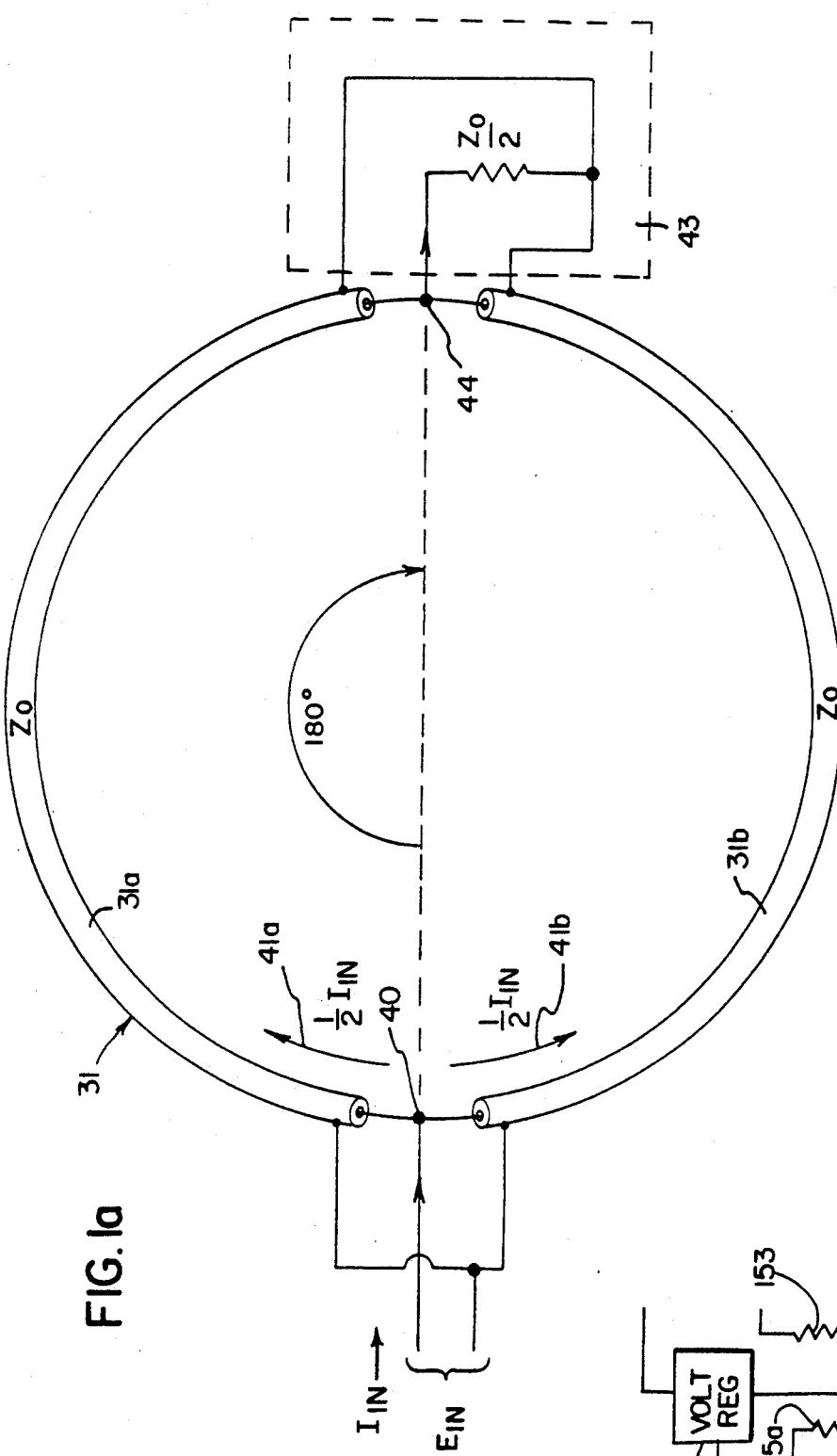
FIG. 1a is a schematic diagram of a slip ring modeled as a high frequency transmission line.

Referring now to FIG. 1a, the slip rings 31 are modeled as two equal length transmission lines 31a and 31b, each having a characteristic impedance of $Z_o$ and each comprising half of the ring 31. In the actual embodiment described below, it will be understood that the actual slip rings 31 are parallel, curvilinear conductors which are more akin to twin-lead or multiple-lead transmission lines. However, the coaxial representation in FIG. 1a is nevertheless used for illustrative purposes.

When high frequency energy is applied at a single drive point 40 on the slip rings 31, the energy divides and propagates around transmission lines 31a and 31b in both directions simultaneously, e.g. in a clockwise direction represented by arrow 41a and in a counterclockwise direction represented by arrow 41b. Theoretically, the effect of high frequency energy propagating around a large diameter slip ring in opposite directions would be the production of interference patterns, such that a signal picked up on the slip ring 31 would be highly position dependent and garbled. This effect is a primary factor in the unsuitability of prior large diameter slip rings for high speed communications.

In the present invention, a termination circuit or terminator 43 contacts the slip ring 31 through another set of brushes at a termination point 44, 180° opposite from the driving point 40. By placing the terminator 43 at the 180° point 44, the divided energy traveling around the ring 31 in opposite directions meets essentially simultaneously at the terminator 43. The terminator 43 is a resistive termination having a resistance value approximately equal to $Z_o/2$ so that the parallel combination of both transmission lines 31a and 31b is matched to the terminator 43, with no reflected energy. And because the path lengths of the two transmission lines 31a and 31b are approximately equal, energy originating at the drive point 40 arrives at the terminator 43 in unison so that there is no continued propagation through to the opposite transmission line 31b or 31a, respectively.

In considering the points of contact for the brushes utilized in this embodiment, it should be noted that conventional brushes are utilized which customarily employ multiple spring loaded leaves which contact the slip ring at multiple, closely spaced points. The multiple leaf brush assemblies are used for reliability of the sliding connection. Even though a multiple leaf brush assembly actually makes multiple points of contact, the multiple points are close enough to each other, as compared to the large slip ring circumference, that they may be considered functionally as a single point. Of course, single leaf brushes are also usable with this invention, in which case there is only one actual point of contact per brush. In the discussion which follows, therefore, the term "point" is understood to mean one or more closely spaced points of contact by a brush assembly.

Referring again to FIG. 1, the above described split transmission line analogy is applied in two different ways in the below described embodiments. A first embodiment relates to an inbound communications path, in which an inbound drive circuit 45 slidably connects to the slip rings 31 via brushes (not shown in FIG. 1). An inbound termination circuit 46 connects to the slip rings 31, also via brushes, at a point 180° opposite the point of connection of the inbound drive circuit 45. The inbound drive circuit 45 receives a serial input signal from the stationary electronics 30 over an input cable 47. The input signal is amplified and transmitted onto the slip rings 31. As in the transmission line model described above, the transmitted energy divides and propagates around the slip ring 31 in two different directions and is terminated at the 180° point. The signal is thus available for reception anywhere on the slip ring 31.

The inbound communications path is completed by an inbound receive circuit 48 and an inbound matching receive circuit 50. The inbound receive circuit 48 is mounted on the rotating gantry 11 and is physically connected to a fixed point on the slip rings 31. The inbound receive circuit picks up the signal transmitted by the inbound drive circuit 45, buffers it, and couples it to the control section 27 via cable 49. The inbound matching receive circuit 50 is also mounted on the rotating gantry 11 and is physically connected to a fixed point on the slip ring 31. The inbound matching receive circuit 50 is approximately identical in circuitry to the inbound receive circuit 48 and is located 180° opposite the inbound receive circuit. The inbound matching receive circuit 50 provides capacitance that is equal to the capacitance of the inbound receive circuit 48 assuring that signal delays in both transmission paths of the slip ring are equal thus avoiding any signal reflection at the inbound termination circuit 46 which would reduce the achievable data transmission rates. Note that since the entire gantry 11 rotates with respect to the stationary brushes associated with the inbound drive and terminate circuits 45 and 46, respectively, the actual position of the inbound receive circuit 48 and the inbound matching receive circuit 50 with respect to the stationary circuits 45 and 46 may be anywhere along the slip ring 31, with the inbound receive circuit 48 and the inbound matching receive circuit 50 remaining diametrically opposed to one another at all times.

Still referring to FIG. 1, a second embodiment relates to an outbound communications path from the control section 27 on the gantry 11 back to the stationary electronics 30. In this second embodiment, the drive and terminate connections are made physically on the slip rings 31 and the receive and matching receive connections are by way of brushes. Specifically, for outbound communications a serial signal is coupled from the control section 27 to an outbound drive circuit 55 over cable 56. Since the outbound drive circuit 55 is located on the gantry 11, a physical connection is made from the outbound drive circuit 55 to the slip ring 31. To provide the above described termination for the drive signal originate by the outbound drive circuit 55, an outbound terminate circuit 57 is likewise physically connected to the slip ring 31 at a point 180° across from the connection for the outbound drive circuit 55. Then, a stationary outbound receive circuit 58 connects to the slip ring 31 via brushes, and couples the received signal to the stationary electronics 30 over cable 59. A stationary outbound matching receive circuit 60 is also connected to the slip ring 31 via brushes and is approximately identical in circuitry to the outbound receive circuit 58. With approximately identical circuitry, the outbound matching receive circuit 60 provides capacitance equal to that of the outbound receive circuit 58 insuring that the delays in signal transmission along both paths of slip ring 31 are equal, thus insuring that substantially no signal energy is reflected.

Again referring to FIG. 1, other aspects of the invention include control of noise on the slip rings an preservation of electrical isolation between the stationary electronics 30 and the control section 27. For these reasons, a separate, independent and isolated d.c. power supply 65 is provided for powering both the inbound and outbound communications circuits. As will be described in detail below, separate slip rings are provided (although not shown separately in FIG. 1) for the communications signals, referred to as signal slip rings, and for the d.c. supply voltages, referred to as power supply slip rings. The power supply slip rings conduct the d.c. supply voltage among the various drive, terminate, receive and matching receive circuits. Specifically, the supply voltages are fed in sequence; (a) from the power supply 65 to the inbound drive circuit 45 via cable 66, (b) from the inbound drive circuit 45 to the inbound receive circuit 48 and the inbound matching receive circuit 50 via a first set of power supply slip rings (not shown separately in FIG. 1), (c) from the inbound receive circuit 48 to the outbound drive circuit 55 via cable 67, and (d) from the outbound drive circuit 55 to the outbound receive circuit 58 and the outbound matching receive circuit 60 via a second set of power supply slip rings (also not shown separately in FIG. 1). Both termination circuits 46 and 57 also have access to the relevant power supply slip rings for use as a sink in terminating the respective signal slip rings. Finally, since the power supply has essentially zero impedance, both power supply slip rings are at a.c. ground potential. The power supply slip rings are therefore interleaved with the signal slip rings in order to enhance transmission line properties and mitigate against interference. Yet another benefit of this power supply distribution and isolation is the rejection of common mode noise. Since the power supply conductors follow principally the same path in parallel with the signal conductors, external noise induces similar voltages in both power and signal lines. As a result, substantial noise immunity and common mode rejection are provided, even utilizing less expensive single ended drive and receive components, as described below.

DESCRIPTION OF THE PREFERRED EMBODIMENT

Figure 2:
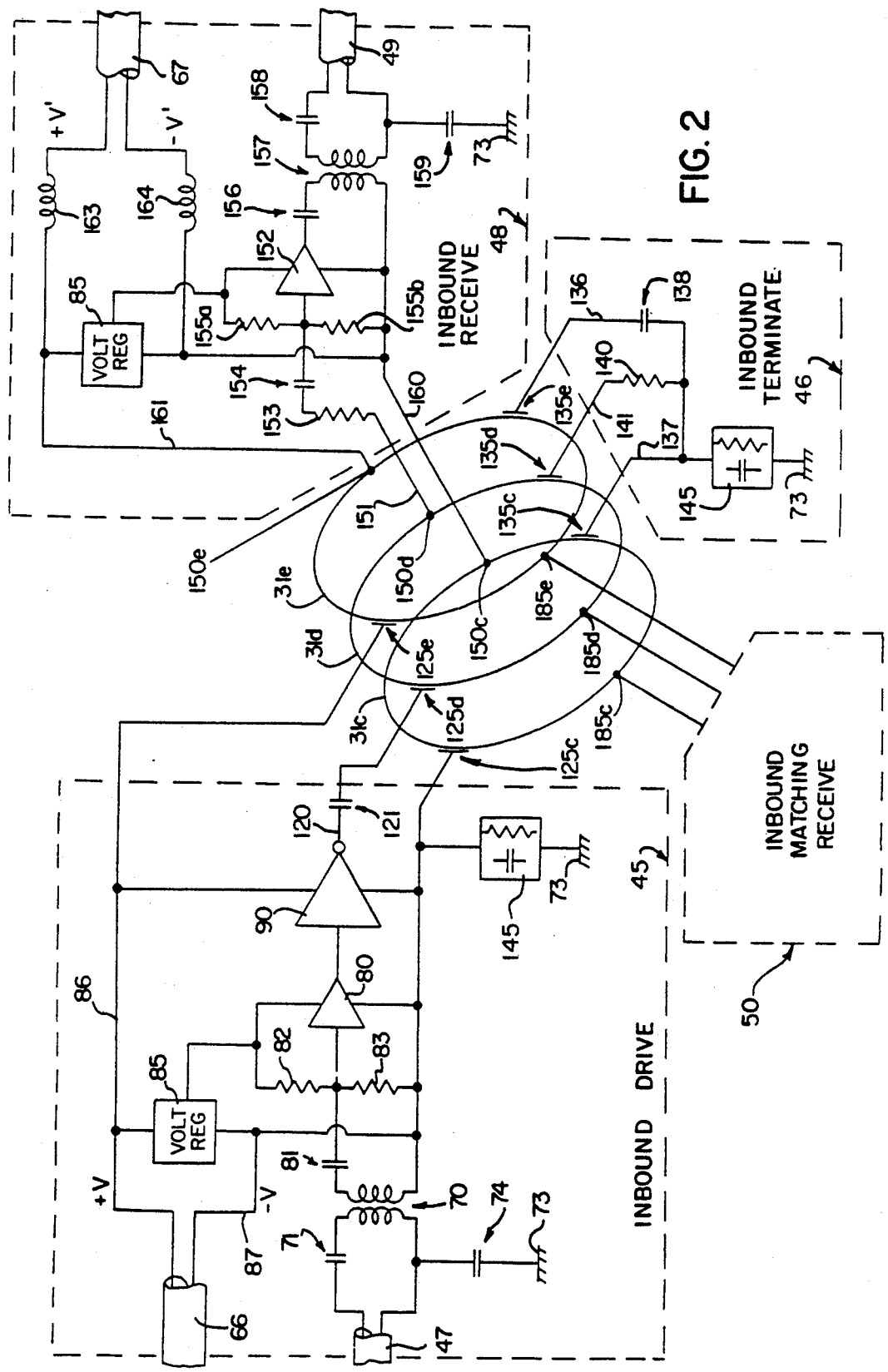
FIG. 2 is a schematic diagram of the inbound communication circuit which forms a part of the high speed communication apparatus of FIG. 1.

Referring to FIG. 2, the serial input cable 47 comprises a pair of conductors 47a and 47b connecting to the inbound drive circuit 45. The serial input signal on line 47 is a high data rate, NRZI encoded signal. The actual encoding in the stationary electronics 30 is performed by an integrated circuit encoder (not shown), type AM7968 manufactured by Advanced Micro Devices. Decoding upon reception in the control circuit 27 is performed by a mating device (not shown), type AM7969, also from Advanced Micro Devices. The same type encoding and decoding devices are also used for outbound communications described below.

The input signal on line 47 is connected to a primary winding of an input transformer 70 through coupling capacitor 71. The transformer 70 provides d.c. isolation for the remainder of the inbound drive circuit 45, as well as inhibiting the formation of a.c. ground loops. Capacitor 71 functions to block d.c. currents which may otherwise saturate transformer 70.

The primary for transformer 70 is also by-passed to chassis ground 73 through capacitor 74. It will be understood from the description below that control of noise, particularly at high frequencies, is an important part of this invention. The chassis ground connection 73 is made to the metal parts comprising the structural frames for the CAT scanner 10. By thus referencing all stages of the communication path to chassis ground 73, system noise is substantially reduced. Capacitor 74 places the primary of transformer 70 at chassis ground 73 for high frequency a.c. signals.

The secondary of transformer 70 is coupled to the input of a pre-driver stage 80 through coupling capacitor 81 and a biasing network formed by resistors 82 and 83. The pre-driver 80 is preferably formed from cascaded standard CMOS integrated circuit inverters, with one input inverter feeding three parallel output inverters. The non-inverting pre-driver 80 thereby formed is used preserve signal symmetry on positive and negative transitions, i.e. equal delay for both polarities of transition. A single CMOS octal inverter/driver integrated circuit type 74AC11240 is utilized to form the pre-driver 80.

Supply voltage for the pre-driver 80 is derived from the supply voltage input cable 66 through a voltage regulator 85. The supply voltage input 66 comprises a single regulated d.c. input voltage of 12 volts labelled $+V$ and $-V$ on lines 86 and 87, respectively. Line 87, $-V$, is used as a common line for the amplifier stages in the inbound drive circuit 45. The input for regulator 85 is tapped from $+V$ on line 86. The regulator 85 is used primarily to permit the operation of the pre-driver circuit 80 at the standard logic voltage of 5 volts, while the the subsequent stage uses the full supply voltage to achieve a larger peak-to-peak output signal voltage. Additionally, since the supply voltage is fed serially to all of the communications drivers 45 and 55 and receivers 48 and 58, it is subject to some ohmic voltage drop, and may also contain substantial spikes induced by switching transients. The separate regulator 85 provides a stable noise free voltage for the pre-driver 80 to prevent false state changes. It should be appreciated by those skilled in the art that the voltage regulator 85 is understood to include input and output bypass capacitors for filtering purposes.

The output of pre-driver 80 is fed to the input of a driver stage 90. The driver stage 90 is connected to the full supply voltage on lines 86 and 87. The driver 90 must have sufficient capability to drive a load equal to the net impedance of the slip ring 31b as seen at the driving point. From the above described transmission line analogy, the net impedance at the driving point can be seen to be half of the impedance of either of the two parallel paths around the rings. For the slip rings 31c-31e in this embodiment, the net impedance has been determined empirically to be approximately 20 ohms (e.g. corresponding to a value of 40 ohms for the impedance of each branch, or $Z_o$, in the analogy of FIG. 1a). Therefore, the driver 90 must drive into an effective impedance of 20 ohms. Since the requirements for both high speed operation and a high drive capability are not currently available in integrated circuit form, the driver 90 is preferably formed from discrete components as shown in U.S. Pat. No. 5,018,174.

An important characteristic of driver 90 is that, in addition to possessing sufficient drive capacity, the output impedance of the driver 90 is matched to the net impedance of the slip rings as seen at the driving point. The matching at the driving point, in addition to the above described matched termination, serves to further reduce any reflected energy, for example, from irregularities or an imperfect match at the termination, or from loading at the receive connection.

Referring again to FIG. 2, the output of driver 90 on line 120 is coupled through capacitor 121 to a brush 125d contacting slip ring 31d. Slip rings 31c and 31e are disposed coaxially and on either side of slip ring 31d. Slip ring 31c is connected to $-V$ via brush 125c, and slip ring 125e is connected to $+V$ through slip ring 125e. Since both $+V$ and $-V$ are low impedance sources, both rings 31c and 31e provide a ground plane for the signal on the center slip ring 31d, thereby providing the desired transmission line effect as well as some degree of shielding against noise and crosstalk. The three slip rings 31c-31e depicted in FIG. 2 are shown with an exaggerated axial separation for simplicity of illustration. In the preferred form, each ring 31c-31e is approximately 3/16 inch in width, with an insulator of approximately 1/16 inch between them.

Still referring to FIG. 2, the inbound terminate circuit 46 connects to the slip rings 31c-31e through brushes 135c-35e, respectively. Each of the brushes 135c-135e is positioned at a point diametrically across the slip rings 31c–31e from the corresponding drive brush 125c–125e. In other words, the drive and terminate brushes 125c–125e and 135c–135e are 180° opposite each other around the slip rings 31c–31e, respectively. Brushes 135c and 135e couple to the −V and +V supply voltages on slip rings 31c and 31e, respectively. The inbound communication signal on slip ring 31d is coupled by brush 135d. In the inbound terminate circuit, the +V supply voltage on line 136 is by-passed to the −V supply voltage on line 137 by capacitor 138, ensuring a low a.c. impedance to signal ground potential, i.e. −V on line 137. A terminating resistor 140 is connected to the signal line 141, and has a value equal to the net impedance seen at the slip rings 31c–31e. As previously explained, the net impedance of the rings, and therefore the preferred value for the terminating resistor, is approximately 20 ohms.

In practice, both the terminating resistor 140 and bypass capacitor 138 are preferably formed as multiple parallel devices in order to decrease the net parasitic inductance and, in the case of the resistor 140, provide increased power dissipation.

The −V supply voltage in each of the inbound drive and inbound terminate circuits 45 and 46, respectively, constitutes the signal ground reference potential, and is by-passed to chassis ground 73 through a high voltage capacitor/resistor network 145 at both brushes 125c and 135c. As mentioned above, by-passing to chassis ground 73 is important for the control of system noise. In particular, since the drive and terminate circuits 45 and 46, respectively, are isolated with respect to d.c., it has been found that by-passing to chassis ground 73 is essential for satisfactory system operation. In addition, since all brushes and slip rings are "floating" with respect to d.c., it is necessary to present a high resistance path between the brush/slip ring system and chassis ground 73 as a d.c. reference and to prevent static charge buildup. The high-voltage capacitor resistor networks 145 therefore include a resistance element in parallel with the capacitor. A preferred construction of this network is shown in U.S. Pat. No. 5,018,174 issued to Collins.

The networks 145 are preferably further formed to have a very high voltage breakdown rating. The reason for the high voltage rating is that in the preferred form, the rings 31c–31d are part of an assembly of a plurality of other slip rings, including three slip rings 31f–31h for the outbound communication circuit as described below, and a set of high voltage rings (not shown) for powering other equipment on the gantry 11, particularly the X-ray tube 15. Because of the proximity of the high voltage rings on the same assembly, a short circuit may develop, for example, between the high voltage source and rings 31c–31e or associated brushes 125c–125e and 135c–135e. If such a short were to occur, a voltage on the order of 1,000 volts may be impressed upon any of the rings 31c–31e. Since the supply voltages +V 83 and −V 87 are ungrounded, e.g. "floating", the imposition of a high voltage fault would not in itself cause component damage, as long as the by-pass networks 145, the coupling transformers 70 of the inbound drive circuit 45 and 157 of the inbound receive circuit 48, and the "floating" range of the power supply 65 itself, are appropriately rated.

Once more referring to FIG. 2, the inbound receive circuit 48 is located on the gantry 11 and rotates along with the slip rings 31c–31e. Therefore, the inbound receive circuit physically connects to the rings 31c–31e at points 150c–150e, which are approximately collinear.

A signal line 151 connects to signal ring 31d and is coupled to the input of buffer 152 through series resistor 153, coupling capacitor 154 and bias resistors 155a and 155b. It is important that the signal line 151 present as high an impedance as possible so as to minimize reflections at the point of connection 150d on slip ring 31d. Preferably, the bridging impedance, i.e. the impedance of signal line 151, as seen at point 150d should be at least ten times greater than the characteristic impedance $Z_o$. In the present embodiment, with $Z_o$ approximately equal to 40 ohms, the bridging impedance at point 150d should therefore be greater than 400 ohms. Even though the buffer 152 has a very high d.c. input impedance, it does have some input capacitance which presents a lower a.c. impedance. Series resistor 153 is therefore used to increase the impedance that line 151 presents at point 150d. A value of 200 ohms for resistor 153 has been found to be satisfactory.

The output of buffer 152 is coupled through capacitor 156 to the primary of coupling transformer 157. The secondary of transformer 157 couples through capacitor 158 to serial output cable 49, which in turn couples the inbound serial data to the control section 27. One leg of coupling transformer 157 is by-passed to chassis ground 73 through capacitor 159. The transformer output coupling, like that described above in relation to the inbound drive circuit 45, both provides d.c. isolation for the brush/ring system and inhibits the formation of a.c ground loops.

Besides the above described data transmission function, the inbound receive circuit 48 also supplies d.c. operating voltage for the outbound communication path. The supply voltages −V and +V are picked up by leads 160 and 161 at connection points 150c and 150e on slip rings 31c and 31e, respectively.

A voltage regulator 85 connects to the +V and −V supply voltages on lines 161 and 160, respectively, and is used to provide a regulated supply voltage for buffer 152 and its associated bias resistors 155a and 155b. The +V and −V supply voltages are also fed through inductors 163 and 164 to produce voltages +V' and −V', respectively. The +V' and −V' designations are used to acknowledge the a.c. decoupling effects afforded by inductors 163 and 164. As described below, the +V' and −V' supply voltages are connected to cable 67 to supply operating power for the outbound communication path as described below.

Figure 3:
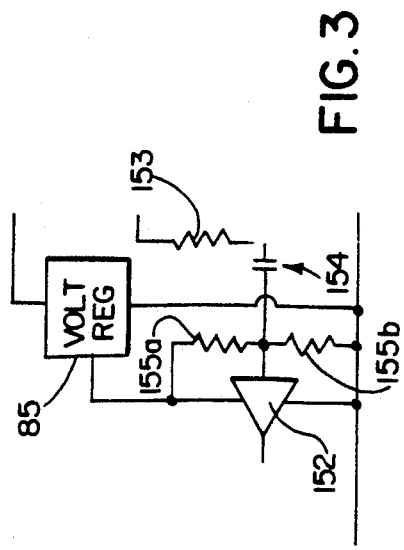
FIG. 3 is a detailed schematic diagram of the matching receiver which forms a part of the inbound and outbound communication circuits of FIGS. 2 and 4, respectively.

Still referring to FIG. 2, the inbound matching receive circuit 50 is located on gantry 11 and is physically connected to the slip rings 31c–31e at points 185c–185d which are approximately collinear. Thus, the inbound matching receive circuit 50 rotates along with the slip rings 31c–31e at a point diametrically opposite the inbound receive circuit 48. As shown in FIG. 3, the inbound matching receive circuit is substantially identical to the inbound receive circuit 48. The values of the resistors 153, 155a and 155b are the same values as the corresponding elements in the receive circuit 48 described above. The same is true of the capacitor 153 and amplifier 152. With identical circuitry, the inbound matching receive circuit 50 causes a delay on its half of the slip ring 31d of the signal transmission which is equal to the delay caused by the inbound receive circuit 48 on its side of the slip ring 31d. With equal delay periods on both paths of the slip ring 31d, there will be no energy reflected from the terminator 43 thus enabling higher data transmission rates to be used.

Figure 4:
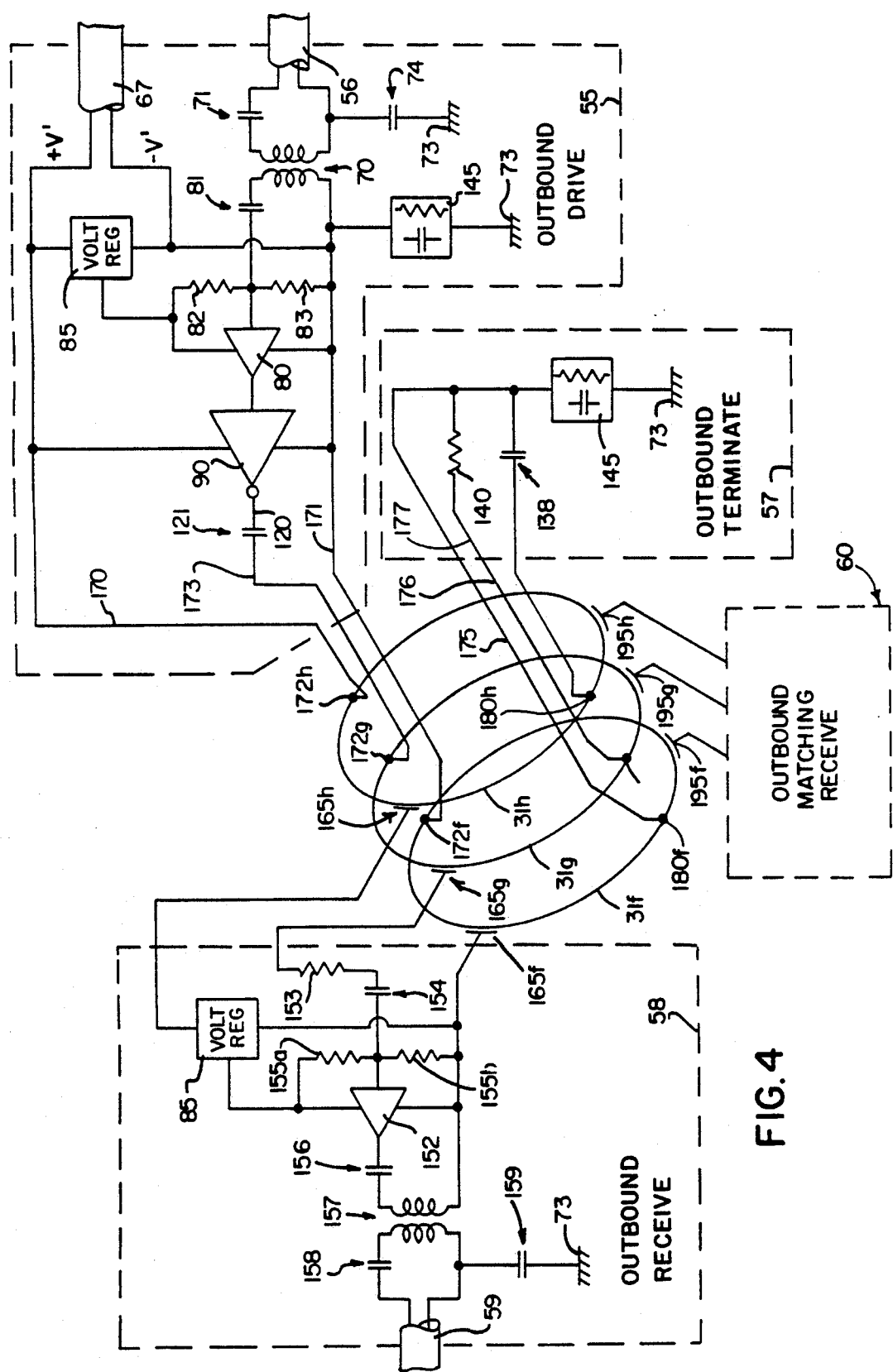
FIG. 4 is a schematic diagram of the outbound communication circuit which forms a part of the high speed communication apparatus of FIG. 1.

Referring to FIG. 4, the outbound communication path illustrates a second embodiment of the invention. In this embodiment, the outbound drive circuit 55 and the outbound terminate circuit 57 are mounted on the rotating gantry 11, and so are connected physically to second set of coaxial slip rings 31f-31h. The outbound receive circuit 58 is stationary and connects to the slip rings 31f-31h via brushes 165f-165h. The outbound matching receive circuit 60 is stationary and connects to the slip rings 31f-31h via brushes 195f-195h. In this embodiment, the principle of terminating the applied signal to a point 180° opposite the driven point is illustrated with both the drive and terminate points being established by physical connection to the slip ring 31, rather than by brushes as in the first embodiment described above. In addition, the outbound receive 58 circuit and the matching receive circuit 60 connections are established by brushes rather than by physical contract to slip ring 31 as in the first embodiment.

The circuitry of the outbound drive, terminate, receive and matching receive circuits 55, 57, 58 and 60 respectively are for the most part identical to the corresponding inbound drive, terminate, receive and matching receive circuits, 45, 46, 48 and 50 respectively, with identical components being indicated by like numerals. Because of the similarity in structure and function of the inbound and outbound circuits, only the differences are described in further detail.

The outbound drive circuit 55 receives the +V' and −V' operating voltages from the inbound receive circuit 48 on cable 67. Conductors 170 and 171 for the +V' and −V' supply voltages are physically connected to slip rings 31f and 31h at points 172f and 172h, respectively. The outbound communication signal is received from the control section 27 on input cable 56. The serial output signal from the outbound drive circuit 55 on line 173 is applied to a physical connection point 172g on slip ring 31g, with all connection points 172f-172h being approximately collinear.

Conductors 175-177 connecting to the outbound terminate circuit 57 make physical contact with slip rings 31f-31h at collinear points 180f-180h. The connection points 180f-180h for the outbound terminate circuit 57 are placed 180° opposite the connection points 172f-172h for the outbound drive circuit 55 according to the above described principles of the invention.

The stationary outbound receive circuit 58 couples to the slip rings 31f-31h via brushes 165f-165h, respectively, thereby receiving the communications signal on ring 31g and the −V' and +V' supply voltages on rings 31f and 31h, respectively. The communications signal is detected as described above and coupled to the stationary electronics 30 via cable 59. It should be noted that the power supply path does not extend beyond the outbound receive circuit 58, thereby avoiding the formation of a ground loop which may otherwise be susceptible to oscillation or noise coupling.

The stationary outbound matching receive circuit 60 couples to the slip rings 31f-31h via brushes 195f-195h respectively, thereby receiving the communication signal in ring 31g and the −V' and +V' supply voltages in rings 31f and 31h respectively. Its compound values are selected to match those of the corresponding components in the outbound receive circuit 58.

As a final note on layout, due to the high frequencies involved, it is preferred that all active circuits be physically placed as close as possible to their respective connections to the slip rings. Specifically, in the preferred form, both the inbound rings 31c-31e and the outbound rings 31f-31h are arranged adjacent to each other. The inbound drive circuit 45 and the outbound receive circuit 58 are formed on a circuit assembly which is physically located right on a brush assembly comprising the brushes 125c-125e and 165f-165h. The inbound terminate circuit 46 and the outbound matching receive circuit 60 are physically and the outbound matching receive circuit 60 are physically located right on a brush assembly comprising the brushes 135c-135e and 195f-195h respectively. Similarly, the inbound receive circuit 48, the inbound matching receive circuit 50, the outbound drive circuit 55, and outbound terminate circuit 57 are located in the immediate proximity of their respective physical slip ring connections.

It should be apparent to those skilled in the art that numerous modifications of the above described embodiments are contemplated within the scope of this invention. For example, although the slip rings have been described as rotating along with the gantry 11, it is equally possible to instead have the slip rings be stationary, with brushes mounted on the rotating gantry. In the latter case, the brushes may contact the slip rings on an inside circumference. In other words, stationary and rotating mechanical mounting structures can be interchanged.

It is further contemplated by this invention that physical connections to the slip rings in the above embodiments may be replaced by brushes so that, e.g. all contacts with the slip rings are made by brushes. In that way, the slip rings need not necessarily be fixed to any one platform, but may instead be "free wheeling".

Finally, the actual diameter of the slip rings may vary substantially from the approximate four foot diameter indicated in the above embodiments. CAT scanners are also known and used in industrial application, for example, inspecting parts for defects. Such industrial CAT scanners can be made much smaller since they are not required to accommodate a full size human patient. Consequently, much smaller slip rings may be used. In that case, it should still be found that at high data rates, the principles according to the invention are required.

I claim:

1. A communications apparatus for providing high speed communications between first and second electronics systems mounted on first and second mechanical mounting structures, respectively, where the first and second mechanical mounting structures rotate with respect to each other along an axis of rotation, the apparatus comprising:

a slip ring arranged coaxially with the axis of rotation and attached to one of said mounting structures;

drive means attached to the first mechanical mounting structure and electrically connecting the first electronics system to the slip ring at a first point in the frame of reference of the first mechanical mounting structure;

termination means attached to the first mechanical mounting structure and electrically connected to the slip ring at a second point in the frame of reference of the first mechanical mounting structure which is diametrically opposite said first point in the frame of reference of the first mechanical mounting structure;

receive means attached to the second mechanical mounting structure and electrically connecting the second electronics system to the slip ring at a first point in the frame of reference of the second mechanical mounting structure;

matching receive means attached to the second mechanical mounting structure and electrically connected to the slip ring at a second point in the frame of reference of the second mechanical mounting structure which is diametrically opposite said first point in the frame of reference of the second mechanical mounting structure;

wherein the drive means transmits an electrical signal on the slip ring which is received by the receive means, and the matching receive means balances the impedance of the receive means such that any reflection of the electrical signal from the termination means is minimized.

2. The apparatus as recited in claim 1 in which the drive means and the termination means are electrically connected to the slip ring by brushes.

3. The apparatus as recited in claim 1 in which the receive means and the matching receive means are electrically connected to the slip ring by brushes.

4. A communications apparatus for providing high speed communications between first and second electronics systems mounted on first and second mechanical mounting structures, respectively, where the first and second mechanical mounting structures rotate with respect to each other along an axis of rotation, the apparatus comprising:

a first slip ring arranged coaxially with the axis of rotation between the first and second mechanical mounting structures;

drive means mounted on the first mechanical mounting structure and connected to the first electronics system for transmitting an electrical signal voltage onto the first slip ring, the electrical signal voltage being referenced to a signal ground reference potential and being encoded with data to be communicated from the first electronics system to the second electronics system, the drive means -including first connection means for making contact with the first slip ring at a first point in the frame of reference of the first mechanical mounting structures;

termination means mounted on the first mechanical mounting structure for providing termination of the electrical signal voltage on the first slip ring, the termination means including:

second connection means for making contact with the first slip ring at a second point in the frame of reference of the first mechanical mounting structure, the first and second points in the frame of reference of the first mechanical mounting structure being located approximately diametrically opposite each other across the first slip ring; and a resistive termination connected between the second connection means and the signal ground reference potential;

receive means connected to the second electronic system on the second mechanical mounting structure for receiving the electrical signal voltage on the first slip ring, the receive means including third connection means for making contact with the first slip ring at a first point in the frame of reference of the second mechanical mounting structure to receive the electrical signal voltage from the first slip ring; and matching receive means mounted on the second mechanical mounting structure for providing a signal delay approximately equal to that of the receive means, the matching receive means including fourth connection means for making contact with the first slip ring at a second point in the frame of reference of the second mechanical mounting structure to receive the electrical signal voltage from the first slip ring, the first and second points in the frame of reference of the second mechanical mounting structure being located approximately diametrically opposite each other across the first slip ring.

5. The apparatus recited in claim 4 in which:

the first slip ring is mounted on the second mechanical mounting structure in a fixed position with respect to the frame of reference of the second mechanical mounting structure;

the first connection means comprises first brush means adapted for slidable electrical contact with the first slip ring;

the second connection means comprises second brush means adapted for slidable electrical contact with the first slip ring;

the third connection means comprises a physical electrical contact with the first slip ring; and the fourth connection means comprises a physical electrical contact with the first slip ring.

6. The apparatus as recited in claim 1 in which:

the first slip ring is mounted on the first mechanical mounting structure in a fixed position with respect to the frame of reference of the first mechanical mounting structure;

the first connection means comprises a first physical electrical contact with the first slip ring;

the second connection means comprises a second physical electrical contact with the first slip ring;

the third connection means comprises brush means adapted for slidable electrical contact with the first slip ring; and the fourth connection means comprises brush means adapted for slidable electrical contact with the first slip ring.

7. The apparatus as recited in claim 4 in which:

a second slip ring is mounted coaxially with the first slip ring, the second slip ring being arranged adjacent to the first slip ring;

the drive means include fifth connection means for making contact with the second slip ring at a third point in the frame of reference of the first mechanical mounting structure for applying the signal ground reference potential to the second slip ring, with the third point being approximately colinear with the first point along a first line parallel to the axis of rotation; and the termination means include a sixth connection means for making contact with the second slip ring at a fourth point in the frame of reference of the first mechanical mounting structure, with the fourth point being approximately colinear with the second point along a second line parallel to the axis of rotation and with the third and fourth points being approximately diametrically opposite each other across the second slip ring, wherein the signal ground reference potential used for the resistive termination is obtained from the sixth connection means.

8. The apparatus as recited in claim 7 in which the fifth and sixth connection means are coupled to a chassis ground reference potential through a capacitive bypass means.

9. The apparatus as recited in claim 7 in which
a third slip ring is mounted coaxially with the first and second slip rings, the first slip ring being arranged adjacent to and between the second and third slip rings;
the drive means include ninth connection means for making contact with the third slip ring at a fifth point in the frame of reference of the first mechanical mounting structure for applying a power supply voltage to the third slip ring, the power supply voltage being referenced to the signal ground reference potential on the second slip ring, with the first, third and fifth points in the frame of reference of the first mechanical mounting structure all being approximately colinear;
the receive means includes a seventh connection means for making contact with the second slip ring at a third point in the frame of reference of the second mechanical mounting structure, and an eleventh connection means for making contact with the third slip ring at an fifth point in the frame of reference of the second mechanical mounting structure, with the first, third and fifth points in the frame of reference of the second mechanical mounting structure all being approximately colinear, wherein an operating voltage for the receive means is obtained as the voltage between the power supply voltage obtained from the eleventh connection means and the signal ground reference potential is obtained from the seventh connection means; and
the matching receive means include an eighth means for making contact with the second slip ring at a fourth point in the frame of reference of the second mechanical mounting structure, a twelfth connecting means for making contact with the third slip ring at a sixth point in the frame of reference of the second mechanical mounting structure, with the second, fourth and sixth points in the same frame of reference being approximately colinear, the third and fourth points in the same frame of reference being approximately diametrically opposite each other on the second slip ring, the fifth and sixth points in the same frame of reference being approximately diametrically opposite each other on the third slip ring, wherein an operating voltage for the matching receive means is obtained as the voltage between the power supply voltage obtained twelfth connection means and the signal ground reference potential is obtained from the eighth connecting means.

* * * * *